United States Patent [19]
Szelke et al.

[11] Patent Number: 6,096,712
[45] Date of Patent: *Aug. 1, 2000

[54] KININOGEN INHIBITORS

[75] Inventors: Michael Szelke, Romsey; David Michael Evans, Southampton; David Michael Jones, West Mellow, all of United Kingdom

[73] Assignee: Feering B.V., Hoofdorp, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/605,046

[22] Filed: May 16, 1996

Related U.S. Application Data

[66] Substitute for application No. PCT/GB94/01887, Aug. 31, 1994.

[30] Foreign Application Priority Data

Sep. 8, 1993 [GB] United Kingdom .................... 9318637

[51] Int. Cl.⁷ ....................................................... C07K 5/06
[52] U.S. Cl. .............................. 514/19; 514/18; 530/331; 562/56
[58] Field of Search ........................ 514/18–19; 530/331; 562/560

[56] References Cited

U.S. PATENT DOCUMENTS

| | | | |
|---|---|---|---|
| 4,568,636 | 2/1986 | Svendsen | 435/13 |
| 4,713,369 | 12/1987 | Stüber | 514/18 |
| 4,927,809 | 5/1990 | Stüber | 514/20 |
| 5,519,005 | 5/1996 | Lider et al. | 514/19 |

FOREIGN PATENT DOCUMENTS

| | | | |
|---|---|---|---|
| A1 0074787 | 3/1983 | European Pat. Off. . |
| A2 0192135 | 8/1986 | European Pat. Off. . |
| A2 0235692 | 9/1987 | European Pat. Off. . |
| 2085444 | 4/1982 | United Kingdom . |
| WO/92/04371 | 3/1992 | WIPO . |
| WO 92/07869 | 5/1992 | WIPO . |
| WO/93/11152 | 6/1993 | WIPO . |

OTHER PUBLICATIONS

"Inhibition of Thrombin with H–and Boc–D–Phe–Pro–Agm", *Peptides,* 1983, Walter de Gruyter & Co., Berlin • New York.

Experientia, 25/6, pp. 573–574.

Chemical Abstracts vol. 108, p. 1563139 (Braz. J. Med. Biol. Res. 1987, 20(5), 511–520.

J. Biochem 1988, 104, 200–206.

Life Sciences 1985, 37, 1015–1022.

*Primary Examiner*—Bennett Celsa
*Attorney, Agent, or Firm*—Larson & Taylor

[57] ABSTRACT

Kininogenase inhibiting peptides or peptide analogues with C-terminal related to agmatine or noragmatine.

19 Claims, No Drawings

KININOGEN INHIBITORS

This application is a 371 of PCT/GB94/01887 Aug. 31, 1994.

FIELD OF INVENTION

The invention relates to enzyme inhibition and to treatment of disease.

BACKGROUND—KININS

Kinins are natural vasoactive peptides liberated in the body from high molecular weight precursors (kininogens) by the action of selective proteases known as kininogenases.

There is evidence for the involvement of kinins in the following pathological states:

(a) Conditions associated with vasodilatation and hypotension, e.g. septic, anaphylactic and hypovolaemic shock; carcinoid syndrome and dumping syndrome (b) Conditions involving inflammation, e.g. acute arthritis, pancreatitis, local thermal injury, crush injury and brain oedema (c) Conditions involving bronchoconstriction, especially for example the initial, acute allergic reaction in asthma (d) Allergic inflammation, particularly allergic rhinitis and conjunctivitis, together generally known as hay fever, and the bronchial inflammation and consequent occlusion found in the non-acute but serious and even fatal inflammatory phase of asthma.

The kinins (bradykinin, kallidin and Met-Lys-bradykinin) are potent mediators of inflammation. Their main actions are as follows:

(a) They increase capillary permeability which leads to exudate formation and oedema (b) They are potent vasodilators in arterioles and therefore reduce blood pressure and increase blood flow (c) They induce pain (d) They contract bronchial smooth muscle (e) They activate phospholipase $A_2$ and thus stimulate the biosynthesis of prostaglandins (PG's) which mediate some of their actions.

In regard to prostaglandins, it may be noted that certain actions of kinins, particularly pain and vascular permeability above, are potentiated by PG's, although PG's themselves do not cause pain nor do they induce vascular permeability at the concentrations found in inflamed tissue. PG's therefore act as either mediators or potentiators of kinins.

In spite of the above knowledge of kinins and their actions, relatively little attention has been paid to reduction of their action. In asthma treatment for example clinical attention is primarily directed to the acute bronchoconstrictive reaction, for which there are effective drugs. Deaths continue to occur from the gradually developing bronchial occlusion. At present there are no selective inhibitors of kinin release in clinical use, and their potential use in allergic inflammation appears to have been unpublished prior to our PCT application WO 9204371 of Mar. 19, 1992.

BACKGROUND—KININOGENASES

The kininogenases are serine proteinases, that is to say proteinases in which the hydroxy group of a serine residue is the nucleophile involved in forming the substrate transition state. They liberate the kinins (bradykinin, kallidin) from the kininogens by limited proteolysis. There are several kinds of kininogenase:

(a) Tissue kallikrein (TK, also called glandular kallikrein GT or urinary kallikrein UK) which is found in the pancreas, brain, salivary and sweat glands, intestines, kidney and urine. It has MW=30,000 and acts preferentially on low molecular weight kininogen (LMWK) to release the kinin kallidin (KD). Tissue kallikrein has no potent and fast acting endogenous inhibitor present in plasma. Recently it has been established that at least three homologous genes code for TK's. The hPK gene is expressed in the tissues mentioned above. Additionally, the PSA gene encodes a prostate specific TK and the hGK-1 gene expresses a TK in neutrophils.

(b) Plasma kallikrein (PK) occurs in plasma as an inactive zymogen which is activated by Factor XIIa, and is part of the intrinsic coagulation cascade. It has MW =100,000 and its preferred substrate is high molecular weight kininogen (HMWK) from which it releases bradykinin (BK). Plasma kallikrein is rapidly and effectively inhibited in plasma, by endogenous inhibitors known as cl-inactivator and $\alpha_2$-macroglobulin.

(c) Mast cell tryptase (MT) has been found in large amounts in the pulmonary mast cells of asthmatics. MT has been shown to release bradykinin from both LMWK and HMWK and may therefore be of aetiological significance in asthma (as indeed TK appears to be).

BACKGROUND—KININOGENS

The kininogens which are the natural substrates for the kininogenases (they act also as potent inhibitors, Ki approx. $10^{-11}$M, of cysteine proteinases such as cathepsins B, H and L, calpain and papain) occur in two types:

(a) Low molecular weight kininogen (LMWK) with molecular weight in the range 50,000–70,000 depending on species of origin and degree of glycosylation.

(b) High molecular weight kininogen (HMWK) with molecular weight in the range 88,000–114,000 which, in addition to serving as an alternative precursor of kinins and a cysteine proteinase inhibitor, also plays an obligatory role with plasma kallikrein in the initiation of the intrinisic coagulation cascade.

The two kininogens, whose mRNA's are transcribed from the same gene, have identical primary sequences throughout the N-terminal or heavy chain (H-chain) region, the kinin region and the first twelve amino acids of the C-terminal or light chain (L-chain). At this point their structures diverge, HMWK having a longer L-chain (MW approximately 45K) than LMWK (4.8K).

The cleavage of human HMWK by plasma kallikrein is for example shown schematically in FIG. 1, with details of the sequence at the cleavage sites in FIG. 2 and a more detailed sequence in FIG. 3 where the conventional numbering of residues adjacent to a cleavage site is shown for cleavage site I. After excision of one or other kinin sequence, the H- and L-Chains are held together by a single disulphide bridge:

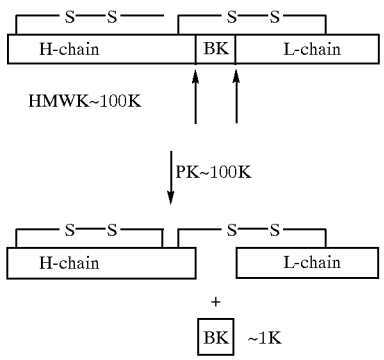

Figure 1. Cleavage of HMWK by PK: Overall scheme

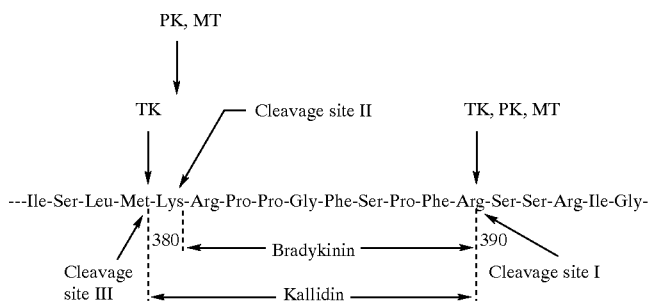

Figure 2. Cleavage of human kininogens by PK and TK: Details of sequence

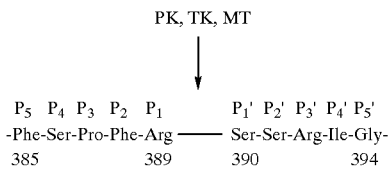

Figure 3. Sequences flanking cleavage site I in human HMWK

As shown, PK, TK and MT act at a single site to free the kinin C-terminal site, cleaving between residues 389 and 390, but at sites one residue apart, either side of residue 380, to free the N-terminal of bradykinin (by PK and MT) or kallidin (by TK).

The role of PK and HMWK as clotting factors in the intrinsic cascade does not involve enzymic cleavage. However many of the effects of PK and probably all those of TK and MT do involve proteolytic cleavages either of kininogens to liberate kinins or of other substrates, e.g. precursors of growth factors.

INDICATIONS

The main clinical indications for kininogenase inhibitors are inflammatory conditions, particularly allergic inflammation (e.g. asthma and hay fever). A fuller list of indications is given below:

(1) Allergic inflammation (e.g. asthma, rhino-conjunctivitis [hay fever], rhinorrhoea, urticaria), excess lung mucus, ascites build-up.

(2) Inflammation (e.g. arthritis, pancreatitis, gastritis, inflammatory bowel disease, thermal injury, crush injury, conjunctivitis), periodontal disease, chronic prostate inflammation, chronic recurrent parotitis, inflammatory skin disorders (e.g. psoriasis, eczema), hepatic cirrhosis, spinal cord trauma and SIRS (systemic inflammatory response syndrome).

(3) Smooth muscle spasm (e.g. asthma, angina), RDS (respiratory distress syndrome).

(4) Hypotension (e.g. shock due to haemorrhage, septicaemia or anaphylaxis, carcinoid syndrome, dumping syndrome)

(5) Oedema (e.g. burns, brain trauma, angioneurotic oedema whether or not as a result of treatment with inhibitors of angiotensin converting enzyme)

(6) Pain and irritation (e.g. burns, wounds, cuts, rashes, stings, insect bites), migraine.

(7) Male contraceptive agents by virtue of inhibition of prostate kallikrein.

(8) Prevention of excessive blood loss during surgical procedures.

(9) Growth factor regulation: TK is implicated in processing of precursors of various growth factors e.g. EGF, NGF.

STATEMENT OF INVENTION

In one aspect the invention provides a method of treatment (including prophylactic treatment) of an inflammatory or other condition set out in the indications above, particularly an allergic inflammatory condition, wherein an effective amount of a peptide or peptide-analogue kininogenase inhibitor as described herein is administered topically or systemically to a patient suffering from or at risk of the condition. It is believed that for optimum activity administrability and stability in the body the compounds should not exceed the size of a hexapeptide, that is to say should not comprise more than six amino acid or amino acid analogue residues; the presence of further residues, particularly in a pro-drug from which residues are cleaved in the body to give the compound primarily exerting the desired effect, is however not excluded.

Particularly, the invention provides a method of treatment of the allergic inflammatory phase of asthma, wherein an effective amount of a kininogenase inhibitor, as described herein, is administered topically or systemically to a patient suffering from or at risk of the condition.

The invention extends further to a method of preparation of a medicament for the topical or systemic treatment (including prophylactic treatment) of conditions as above particularly for allergic inflammatory conditions and especially for asthma as above, wherein a kininogenase inhibitor as described herein is associated with a pharmaceutically acceptable diluent or carrier to constitute said medicament.

In the above, the kininogenase inhibitor is of the novel kind now described whereby in another aspect, without limitation to any particular clinical indication, the invention provides synthetic, low molecular weight compounds that selectively inhibit kininogenases and thus block the release of kinins from kininogens and also block the processing of various growth factors or any other action of these enzymes. The inhibitors are peptides or peptide analogues, desirably (as above) not exceeding the size of a hexapeptide in terms of amino acid or analogue residues.

The inhibitors are essentially of the structure A-B-C, in which A represents the $P_3$ residue, B the $P_2$ residue, C the $P_1$ residue and where A, B are amino acyl or amino acyl analogue groups linked by peptide bonds or conformational analogues thereof giving a peptide mimic, and C is as defined below. Other residues in addition to these essential ones may of course be present, including amino acyl or amino acyl analogue residues.

In particular:

i)

C is:-

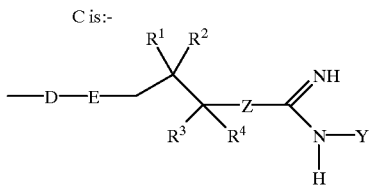

wherein:
Y is —H —$NO_2$ —CN —$CONH_2$ —OH or —$NH_2$; Z is —$CH_2$——NH——S—or —O—;
$R^1$, $R^2$, $R^3$, $R^4$, are —H, alkyl (C1 to C6), —OH, alkoxy, halide, —SH, or —S—alkyl (C1 to C6), or one or both of $R^1R^2$, $R^3R^4$, constitute a carbonyl group or a cycloalkyl (C3 to C6) group; D is —$NR^{11}$—where $R^{11}$=H, lower alkyl C1 to C6 or OH; or $SO_2$, CO, $CH_2$, O or S; or =CH—(when the amide bond between B and C is replaced by —CH=CH—);
E is —$CR^5R^6$—(defined as $R^1R^2$, $R^3R^4$ above); —$NR^{11}$—($R^{11}$ as above); O; or S;
and further, the carbonyl of amino-acyl group B together with D and E may be replaced by a heterocyclic ring e.g. oxazolidine, oxazole, azole, tetrazole, isooxazoline, oxazoline, thiazoline;
ii) A and B, one of which may be absent, are amino acyl or amino acyl analogue residues the same or different and in particular:
A is a) a residue of an amino or imino acid or analogue of L- or preferably D- configuration and preferably selected from Aib; Aic; Ala; Aha(2-aminohexanoic acid, also known as norleucine); Apa; Arg; Atc; Aze; Bta; Cdi; Cha; Cin; Cit; Cpg(cyclopentylglycine); α-Dhn; β-Dhn; Dpn; Glu; 4-Gph; 3-Gph; Har; Hch; Hci; His; Hph; Hyp; Ile; Leu; Lys; Nip; α-Nal; B-Nal; 2-Pal; 3-Pal; 4-Pal; Phe; 4-$CF_3$-Phe; 4-Cl-Phe; 4-CN-Phe; 4-F-Phe; 3-F-Phe; 2-Me-Phe; 4-$NO_2$-Phe; 4-$NH_2$-Phe; 2,4-$Cl_2$-Phe; 3,4-$Cl_2$-Phe or other substituted Phe; Phg; Pic; Pro; β-Pro; 3-Ph-Pro; α-homo-Pro; Pse; Pse(OR) where R=Cl to C10 alkyl; Pyr; Ser; Ser (O"Bu); Tal; Tic; α-Tna; Trp; Tyr; Tyr(Et); Val; optionally with an N-terminal group which may in particular be selected from —HCO, lower alkyl-(C1 to C6)—acyl or aromatic acyl; lower alkyl (C1 to C6)-sulphonyl; alkyl (C1 to C10); $HO_2C(CH_2)_n$-, where n=1 to 3, or esters or amides thereof; amino-acyl; alkyloxycarbonyl; aryloxycarbonyl; R-alkylacyl where alkyl is C1 to C10 and end-group R is selected from guanidino, amidino, benzamidino, guanidinophenyl and amidinophenyl; aryl sulphonyl; or in general a Boc, Z, Fmoc or other protecting group;
b) an N,N-diaikyl—(C1 to C20) substituted, or N,N-[$HO_2C(CH_2)_n$-]$_2$- (n=1 to 3) substituted amino acid preferably of D- configuration and preferably as above;
c) a group as follows (B=absent)

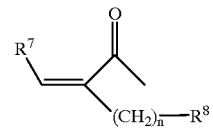

where n=1 to 5; $R^7$=a lipophilic group such as aryl, heteroaryl or alkyl (C1 to C20) and preferably Nap, substituted Nap, cyclooctyl, or decahydronaphthyl; and $R^8$=$R^7$ preferably phenyl (including substituted phenyl) or heteroaryl, and in particular phenylalkyl acyl-, D- or L- aryl- or heteroaryl-alaninyl, or aryl- or heteroaryl- aminoalkyl generally (where 'alkyl' is C1 to C6 and aryl may be substituted);
B is a residue of a liphophilic amino acid or analogue of D- or preferably L-configuration optionally alkyl (C1 to C6) substituted at the B-nitrogen but which is not proline or a proline analogue when $R^1$, $R^2$, $R^3$, $R^4$, $R^5$, $R^6$, $R^9$, $R^{10}$ are all H and may in particular be selected from Ada; Aha; Cha; α-Dhn; β-Dhn; homo-α-Dhn; Hch; Leu; α-Nal; β-Nal; homo-α-Nal; Nse; Phe; 4-F-Phe; 5-F-Phe; Ser(O"Bu); Ser (OBn); homo-α-Tra and where aromatic amino acids may be further substituted in their rings;
iii) further:
the amide function —CONH—between A and B, or B and C (when D =NH), or both may be replaced by a mimetic including —CH=CH—; —CF=CH—; —$CH_2NR^{12}$—where $R^{12}$=H, alkyl, OH; —$COCH_2$—; —$CH(OH)CH_2$—; —$CH_2O$—; —$CH_2S$—; —$CH_2SO_x$—where x=1, 2; —NH CO—; —$CH_2CH_2$—; or heterocyclic rings as under definition of C (when D, E, F may also be encompassed). Such mimetics are well known in the scientific literature especially in the area of peptidomimetic research;
"alkyl" unless otherwise specified encompasses straight-chain, branched and cyclo.

The invention further relates to compounds as represented by C above and their use, both as new compounds and as new elements in pharmaceutically active compounds More particularly, the present invention relates to compounds of the formula:

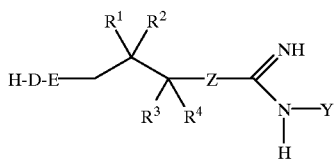

and their protected forms wherein D=NR$^{11}$ where R$^{11}$=H, lower alkyl C1 to C6 or OH; or SO$_2$, CO, CH$_2$, O or S; or =CH—(when the amide bond between B and C is replaced by —CH=CH—); E is —CR$^5$R$^6$—(defined as R$^1$R$^2$, R$^3$R$^4$); R$^1$, R$^2$, R$^3$, and R$^4$ are —H, alkyl (C1 to C6), —OH, alkoxy, halide, —SH, or —S-alkyl (C1 to C6) or one or both of R$^1$R$^2$ and R$^3$R$^4$ constitute a cycloalkyl (C3 to C6) group; but excepting compounds that are an Ω-aminoalkyl guanidine.

The invention also relates to a pharmaceutically active compound comprising a residue of the above-formula but lacking the hydrogen attached to D, or having in the place of that hydrogen a carbonyl group, or having in place of the amide group that is formed by D and such a carbonyl group an amide-group structural mimetic.

In the following, two hundred and sixty six examples of compounds according to the invention are given numbered 101–366 in Table 1, accompanied by a Table of abbreviations. Table 1 is preceded by four detailed examples, concerning in Example 1 the syntheses of compound 101; in Example 2 the synthesis of compound 102, illustrating also the route of synthesis of compounds 103–265 and 358–366; in Example 3 the synthesis of compound 266; and in Example 4 the synthesis of compound 267, illustrating also the route of synthesis of compounds 268–325.

The examples refer further to and are supplemented by eighteen synthesis schemes following them:
Scheme I–Compound 101 (Example 1)
Scheme II–Compound 102 (Example 2, referring therefore also to compounds 103–265 and 358–366)
Scheme III–Compound 266 (Example 3)
Scheme IV–Compound 267 (Example 4, referring therefore also to compounds 268–325)
Scheme V–Compound 326, also illustrating the synthesis of compounds 327, 328
Scheme VI; VII–Compound 329, also illustrating the synthesis of compound 330; compound 331, also illustrating the synthesis of compound 332
Scheme VIII–Compound 333, also illustrating the synthesis of compounds 334–337
Scheme IX–Compound 338
Scheme X–Compound 339, also illustrating the synthesis of compound 340
Scheme XI–Compound 341, also illustrating the synthesis of compounds 342–344
Schemes XII; XIII–Compound 345; compound 346
Scheme XIV–Compound 347
Scheme XV–Compound 348, also illustrating the synthesis of compounds 349, 350
Scheme XVI–Compound 351
Scheme XVII–Compound 352, also illustrating the synthesis of compound 353
Scheme XVIII–Compound 354, also illustrating the synthesis of compounds 355–357

In Table 1 the compounds are given with reference number, structure and molecular ion as determined by FAB (fast atom bombardment) spectrometry. All structure of intermediates were verified by NMR, and where applicable all final products gave satisfactory amino acid analysis.

Kinogenase inhibition assay gave in vitro values in the range $10^{-3}$ to $10^{-9}$ M for the compounds listed in Table I. Activity was further shown in vivo in the well established ovalbumin-sensitised guinea pig model of allergic inflammation.

When the compounds of the present invention are used as a medicine, there are no critical limitations to the administration methods. The present enzyme inhibitor can be formulated by any conventional method in pharmaceutics. For example, the present enzyme inhibitor may be applied in any conventional manner including intravenous injection, intramuscular injection, instillation, oral administration, respiratory inhalation, rhinenchysis, and external skin treatment. Although there are no critical limitations to the administration dosage, the suitable dosage is 1 to 1000 mg/day-person.

EXAMPLE I

101 H-DPro-Phe-Nag

The synthesis of 101 was carried out according to Scheme I. Arabic numerals underlined e.g. 1 refer to structures in these schemes. Roman numerals in parentheses e.g. (i) refer to reaction steps.

(i) Triethylarine (62 mmol) and diphenylphosphoryl azide (62 mmol) were added to a solution of Boc-4-aminobutyric acid (31.3 mmol) in toluene (200 cm$^3$). After 3 hours at 100° C. benzyl alcohol (94 mmol) was added. After a further 18 hours at 100° C. the reaction mixture was washed with 2M NaOH, H$_2$O and brine. The crude product was purified by flash chromatography on silica EtOAc-petrol (1:3).
The pure 1 was isolated as a colourless oil (46%).

(ii) The Boc group of 1 (4.3 mmol) was removed with sat. HCl/Dioxan and the product acylated with Boc-Phe-ONSu (6.45 mmol) in CH$_2$C$_{12}$ (30 cm$^3$) at 0° C. in the presence of N-methylmorpholine. After 3 hours the reaction mixture was worked up using standard procedures and the crude product purified by flash chromatography on silica with EtOAc-petrol (4:6). The pure 2 was isolated as a white solid (99%).

(iii) The Boc group of 2 (4.2 mmol) was removed with sat. HCl/Dioxan and the product acylated with Boc-DPro-ONSu (6.3 mmol) in CH$_2$C$_2$ (30 cm$^3$) at 0° C. in the presence of N-methyl morpholine. After 3 hours the reaction mixture was worked up using standard procedures and the crude product purified by flash chromatography on silica with EtOAc-petrol (13:7). The pure 3 was isolated as a white solid (86%).

(iv) The Z protected amine 3 (3.63 mmol) was hydrogenated over 5% Pd/C in AcOH/H$_2$O (9:1, 40 cm$^3$) at atmospheric pressure and room temperature. After 30 mins the catalyst was filtered off, washed with AcOH/H$_2$O (9:1, 20 cm) and the combined filtrates evaporated in vacuo. The residue was dissolved in dry DMF (10 cm$^3$), the pH adjusted to pH 9 with triethylamine and 3,5-dimethyl pyrazole-1-carboxamidine nitrate (4.0 mmol) was added. After 3 days at room temperature the solvent was removed in vacuo to give the crude guanidine 4 (100%).

(v) The crude guanidine 4 (3.63 mmol) was treated with 2M HCl (30 cm$^3$). After 2 hours at room temperature the solvent was removed in vacuo. The crude material was purified by mplc on *Vydac C$_{18}$ (15–25μ) using MeCN/H$_2$O O/TFA to give pure 101 as a white solid (134 mg). Hplc, *Novapak $C_{18}$, $4\mu$ (8×100 mm), linear gradient 10–50% 0.1% TFA/MeCN into 0.1% TFA/$H_2O$ over 25 min at 1.5 ml min$^{-1}$ indicated a single product ($T_R$=8.8 min). After hydrolysis at 110° C./22 hr with 6N HCl, amino acid analysis Phe 1.03, Pro, 0.97. FAB mass spec [M+H]$^+$=361 (calc. $^m$/Z=360.23).
Trade Name

EXAMPLE II

102 H-DPro-1Nal-Nag (see Scheme II)

(i) 1,3-Diaminopropane (0.3 mol) was converted to the mono-Z diamine hydrochloride 5 by a method outlined in G. J. Atwell and W. A. Denny, Synthesis, 1984, 1032–33.

(ii) Mercuric oxide (63.3 mmol) was added to a solution of 5 (63 mrnol) and N,N' bis Boc-S-methoxyisothiourea (63.3 mmol, R. J. Bergeron and J. S. McManis, J. Org. Chem. 1987, 52, 1700–1703) in ethanol (200 cm³). After 3½ hours at 40° C. the inorganic solid was filtered off and the crude product purified by flash chromatography on silica with EtOAc-petrol (1:9). The pure protected guanidine 6 was isolated as a white solid (94%).

(iii) A solution of 6 (59.5 mmol) and IM HCl (1 equiv.) in methanol (100 cm³) was hydrogenated over 10% Pd/C at atmospheric pressure and room temperature. After 3 hours the catalyst was filtered off. The filtrate was evaporated and the white solid recrystallised (MeOH/$Et_2O$) to give pure 7 (92%).

(iv) H-1Nal-OMe. HCl (60 mmol) was acylated with Boc-DPro-ONSu (84 mmol) in $CH_2Cl_2$ (40 cm³) at 0° C. in the presence of N-methylmorpholine. After 18 hours the reaction mixture was worked up using standard procedures and the crude product purified by flash chromatography on silica with EtOAc-petrol (1:4). Pure 8 was isolated as a white solid (64%).

(v) 8 (38 mmols) was dissolved in THF/$H_2O$ (9:1, 200 cm³). Lithium hydroxide (114 mmols) was added. After 4 hours at room temperature the reaction mixture was worked up to give pure 9 (100%) which was isolated as a white solid.

(vi) The dipeptide 9 (43.5 mmol) and 7 (43.5 mmols) were dissolved in $CH_2Cl_2$/DMF (20:1, 40 cm³). HOBt (52 mmol) and water soluble carbodiimide (52 mmol) were added to this solution at 0° C. After 15 mins the pH was adjusted to pH 8 with N-methylmorpholine. After 18 hours at room temperature the reaction mixture was worked up using standard procedures and the crude product purified by flash chromatography on silica with EtOAc-petrol (4:6). Pure 10 was isolated as a white solid (69%).

(vii) 10 (30 mrnol) was treated with TFA/$H_2O$ (95:5, 50 cm³). After 1.5 hours the solvent was removed in vacuo. The crude material was purified as described in Example I (v). Pure 102 (1.796 g) was isolated as a white solid. Hplc, linear gradient 15→50% 0.1% TFA/MeCN into 0.1% TFA/$H_2O$ over 25 mins at 1.5 ml min$^{-1}$ indicated a single product ($T_R$=10.6 min). FAB mass spec [M+H]$^+$=411.2 (calc. $^m$/Z=410.24).

Compounds 103–265 were also synthesised by this route. Unusual amino acids were synthesised by standard methods. Agmatine based compounds 358–366 were also synthesised by this route.

EXAMPLE III

266 H-DIle-1Nal-Nag (see Scheme III)

(i) 3-Amino-1-propanol (0.33 mol) and di-tert-butyl dicarbonate (0.33 mol) were dissolved in $CH_2Cl_2$ (150 cm³) and the pH was adjusted to pH 9 with diisopropylethylamine. After four hours at room temperature the reaction mixture was worked up by standard procedure to give pure alcohol (11) as a colourless oil (100%).

(ii) Methanesulphonyl chloride (0.36 mol) was added to a solution of 11 (0.33 mol) and triethylamine (0.36 mol) in $CH_2Cl_2$ (200 cm³) at 0° C. After 4 hours the reaction mixture was worked using standard procedures to give the mesylate 12 (100%).

(iii) Sodium azide (1 mol) was added to a solution of 12 (0.33 mol) in dry DMF (100 cm³). After 18 hours at 60° C. the reaction mixture was worked up using standard procedures. The crude product was purified by flash chromatography on silica with EtOAc-petrol (1:9). The pure azide 13 was isolated as a colourless oil (80%).

(iv) The azide 13 (20 mmol) was treated with 4 M HCl/Dioxan (100 cm³). After 30 mins at room temperature the solvent was removed in vacuo and the residue dissolved in EtOH (100 cm³) N,N'-bis-Boc-S-methoxyisothiourea (22 mmol) and mercuric oxide (22 mmol) were added. After 2 hours at 40° C. the reaction mixture was worked up using standard procedures. The crude product was purified by flash chromatography on silica with EtOAc-petrol (1:9). The pure azide 14 was isolated as a white solid (68%).

(v) A solution of the azide 14 (1 mmol) in methanol (40 cm³) and 1M HCl (1 mmol) was hydrogenated over 5% Pd/C at atmospheric pressure and room temperature. After one hour the catalyst was filtered off and the filtrate evaporated in vacuo. The residue was recrystallised from MeOH/$Et_2O$ to give the amine 15 as a white solid (92%).

(vi) Water soluble carbodiimide (0.89 mmol) and HOBt (0.89 mmol) were added to a solution of 15 (0.74 mmol) and Fmoc-1Nal-OH (0.74 mmol) in $CH_2Cl_2$/DMF (9:1, 20 cm³) at 0° C. After 15 mins the pH was adjusted to pH 8 with N-methylmorpholine. After 18 hours at room temperature the reaction mixture was worked up using standard procedures. The crude product was purified by flash chromatography on silica with EtOAc-petrol (3:7). Pure 16 was isolated as a white solid (94%).

(vii) Diethylamine (5 cm³) was added to a solution of 16 (0.69 mmol) in $CH_2Cl_2$ (15 cm³). After 4 hours at room temperature the solvent was removed in vacuo. The residue was acylated with Boc-DIle-ONSu (1.0 mmol) in $CH_2Cl_2$ (30 cm³) at 0° C. in the presence of N-methylmorpholine. After 18 hours the reaction mixture was worked up using standard procedures and the product purified by flash chromatography on silica with EtOAc-petrol (4:6). Pure 17 was isolated as a white solid (54%).

(viii) The protected guanidine 17 (0.35 mmol) was treated with TFA/$H_2O$ (9:1, 10 cm³) for one hour at room temperature. The crude product was purified as described in Example I (v). Pure 266 (50 mg) was isolated as a white solid. Hplc, linear gradient 20→80% 0.1% TFA/MeCN into 0.1% TFA/$H_2O$ over 25 mins at 1.5 ml min$^{-1}$ indicated a single product ($T_R$=8.4 min). FAB mass spec [M+H]$^+$=427.4 (calc. $^m$/z=426.27).

EXAMPLE IV

267 (2-MeO)Ph-CH═CHCO-Nag (see Scheme IV)

(i) H-Nag. (Boc)$_2$. HCl7 (0.17 mmol) was acylated with (2-MeO)Ph-CH═CHCO. ONSu (0.22 mmol) in $CH_2Cl_2$ (10 cm$^3$) at 0° C. in the presence of N-methylmorpholine. After 18 hours the reaction mixture was worked up using standard procedures and the crude product purified by flash chromatography on silica using EtOAc/petrol (1:1). Pure 18 was isolated as a colourless oil (80%).

(ii) 18 (0.136 mmol) was treated with TFA/H$_2$O (9:1, 10 cm$^3$) for one hour at room temperature. Pure 267 (71 mg) was isolated as a white solid. Hplc, linear gradient 10→45% 0.1% TFA/MeCN into 0.1% TFA/H$_2$O over 30 mins at 1.5 ml min$^{-1}$ indicated a single product ($T_R$=19 min). FAB mass spec [M+H]$^+$=277.2 (calc. $^m$/z=276.16).

Compounds 268–325 were also synthesised by this methodology. The required cinnamic acid derivatives were either commercially available or synthesised by standard synthetic methods. See also Scheme XVII

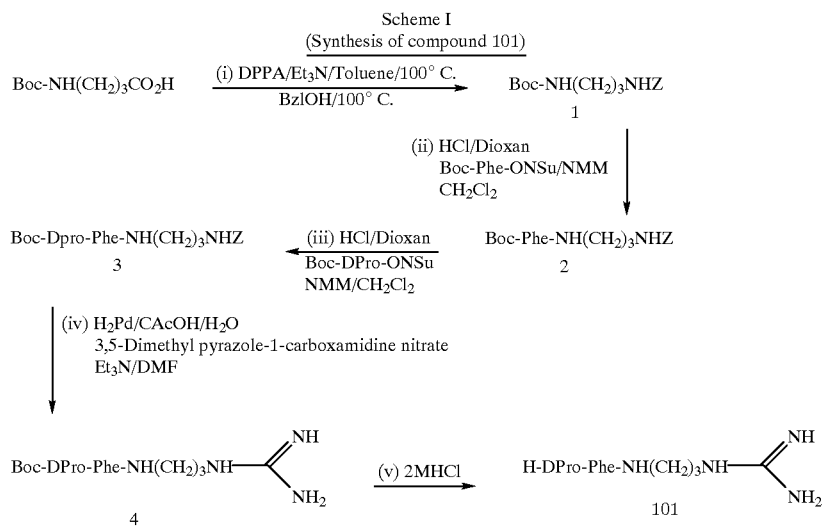

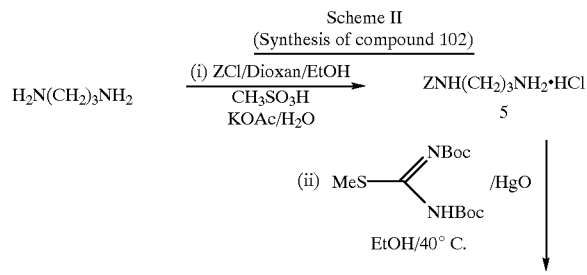

-continued
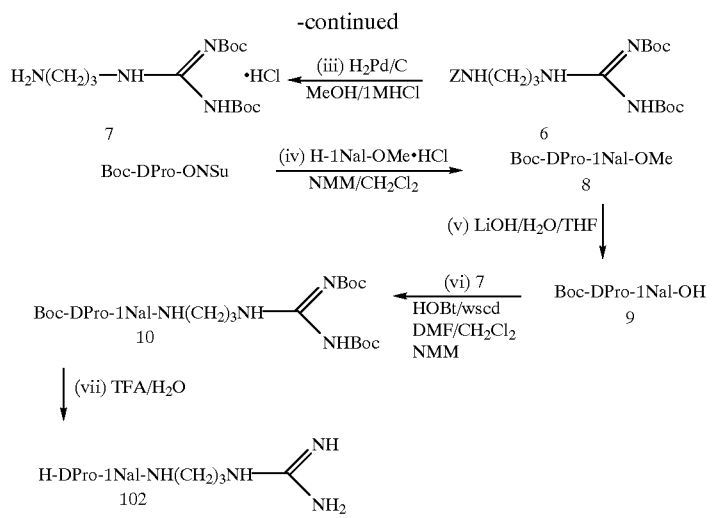
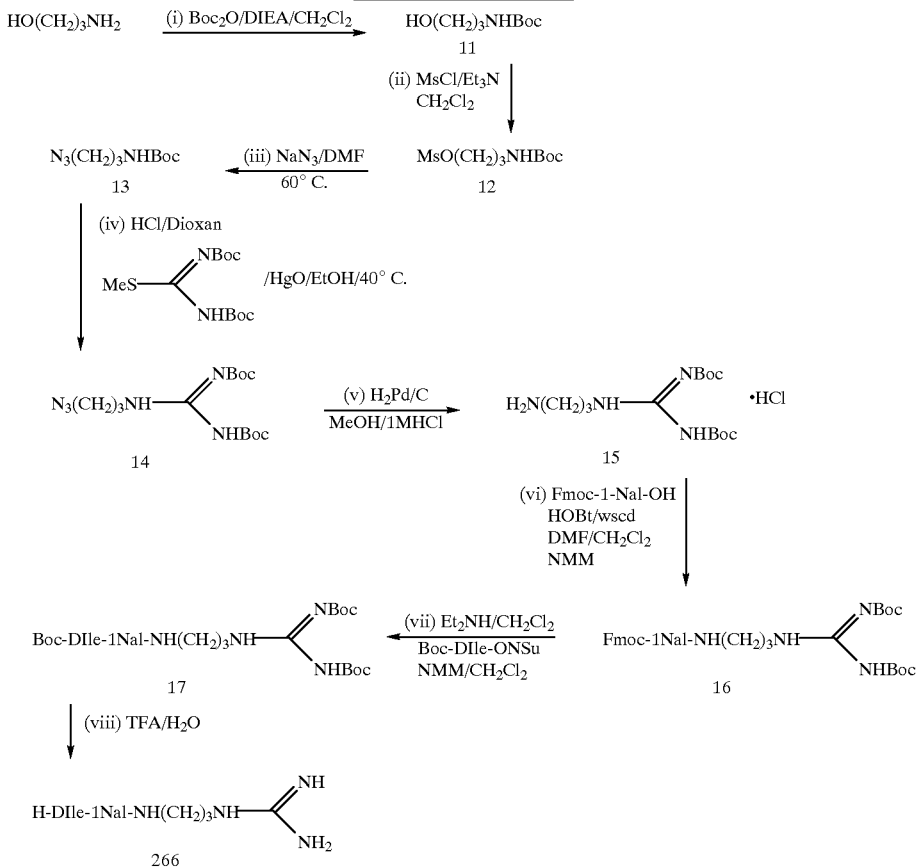

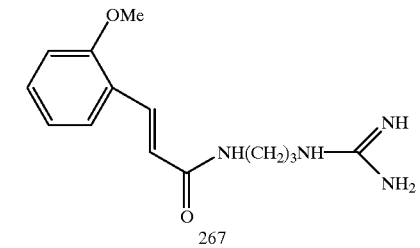
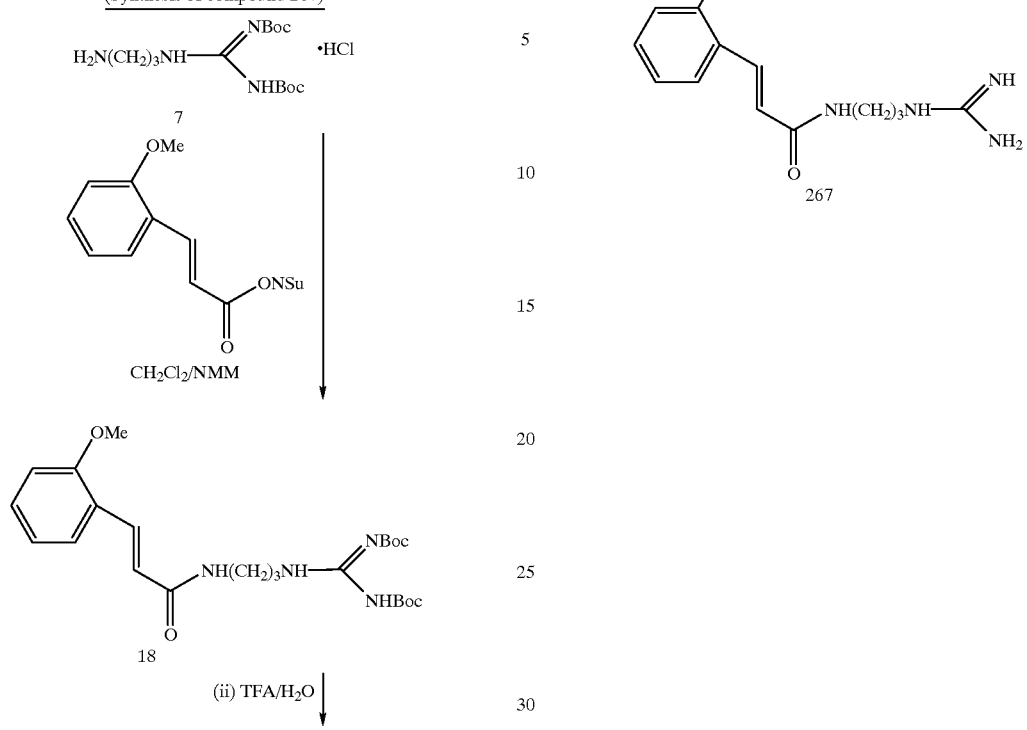

-continued
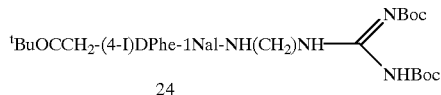
24
↓ (viii) TFA
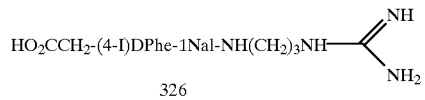
326
Compounds 327 and 328 were also synthesised by this route
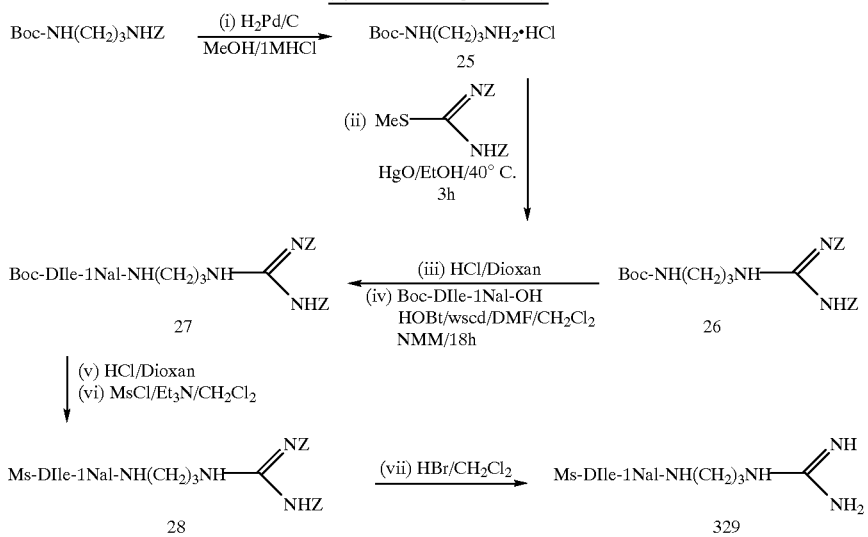
Compound 330 was also synthesised by this route
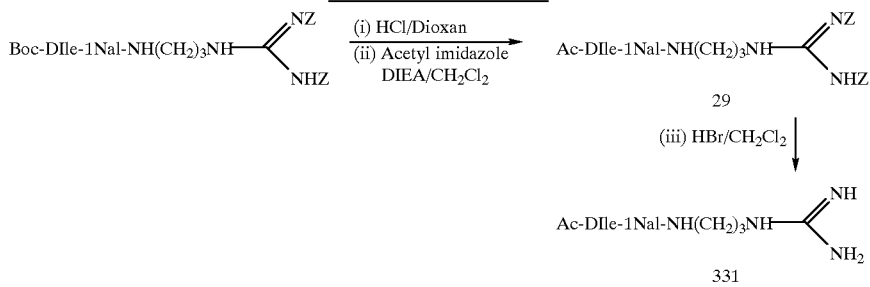
Compound 332 was also synthesised by this route Scheme VIII
(Synthesis of compound 333)
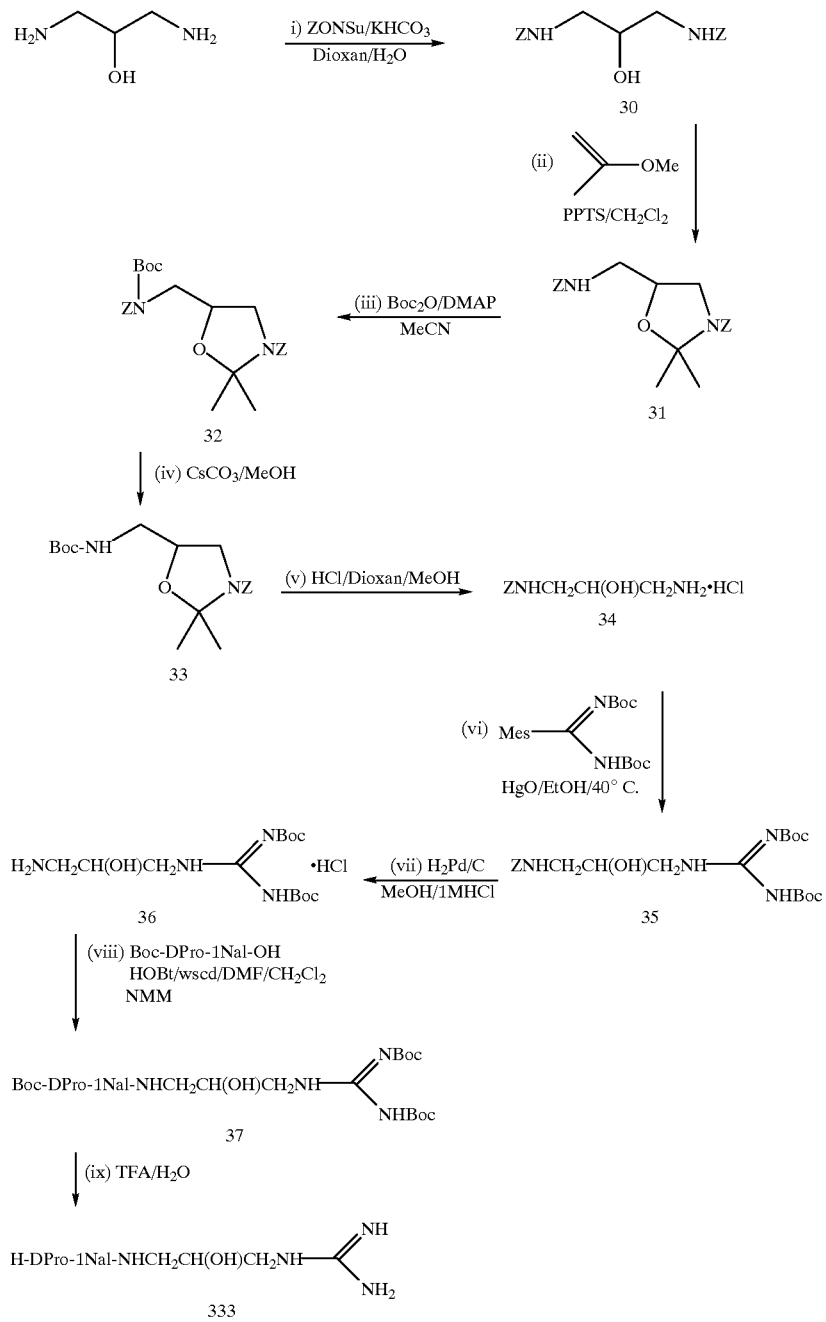
Compounds 334-337 were also synthesised by this route

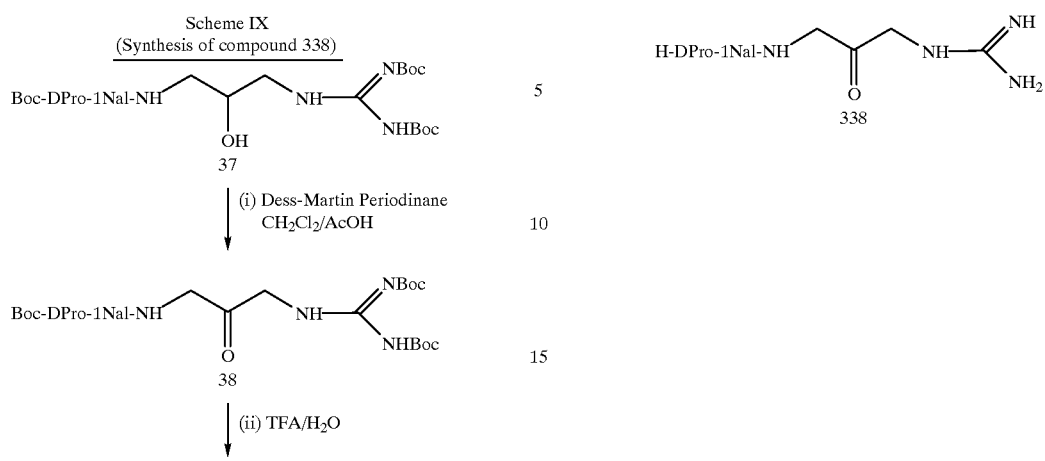
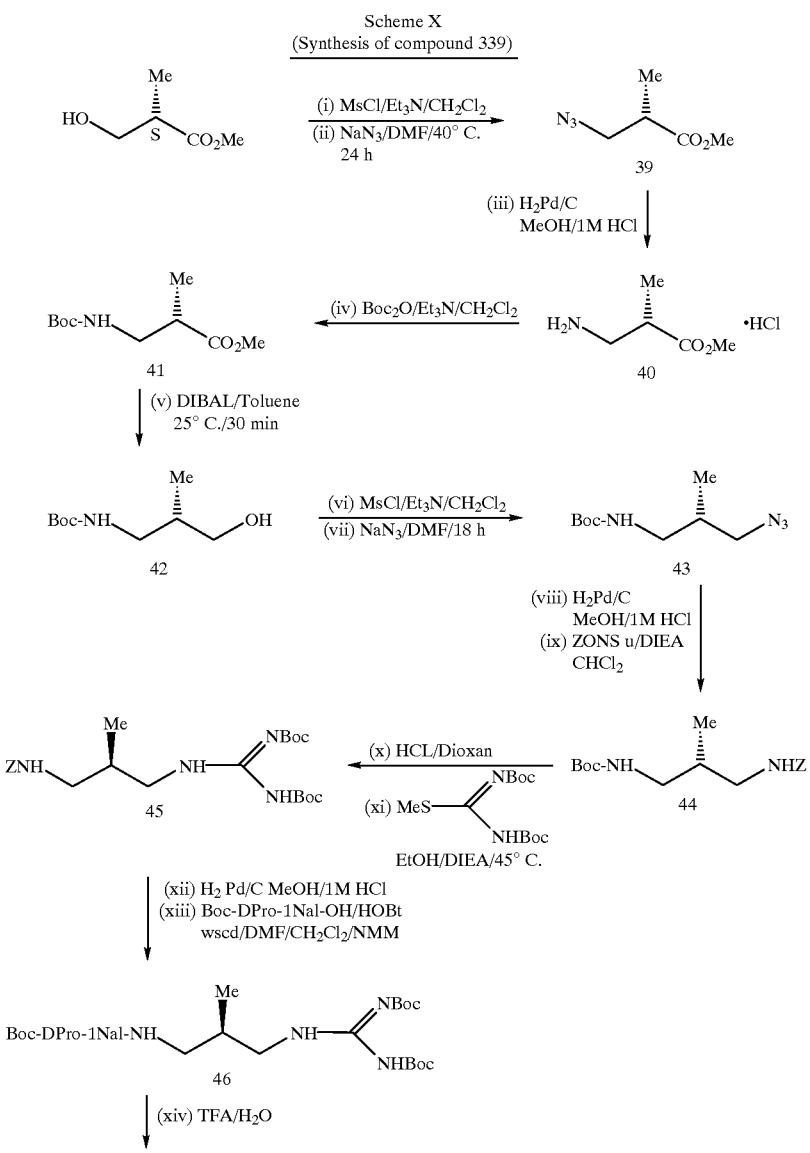

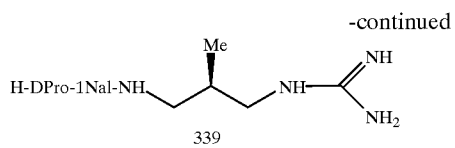
339
Compound 340 was also synthesised by this route
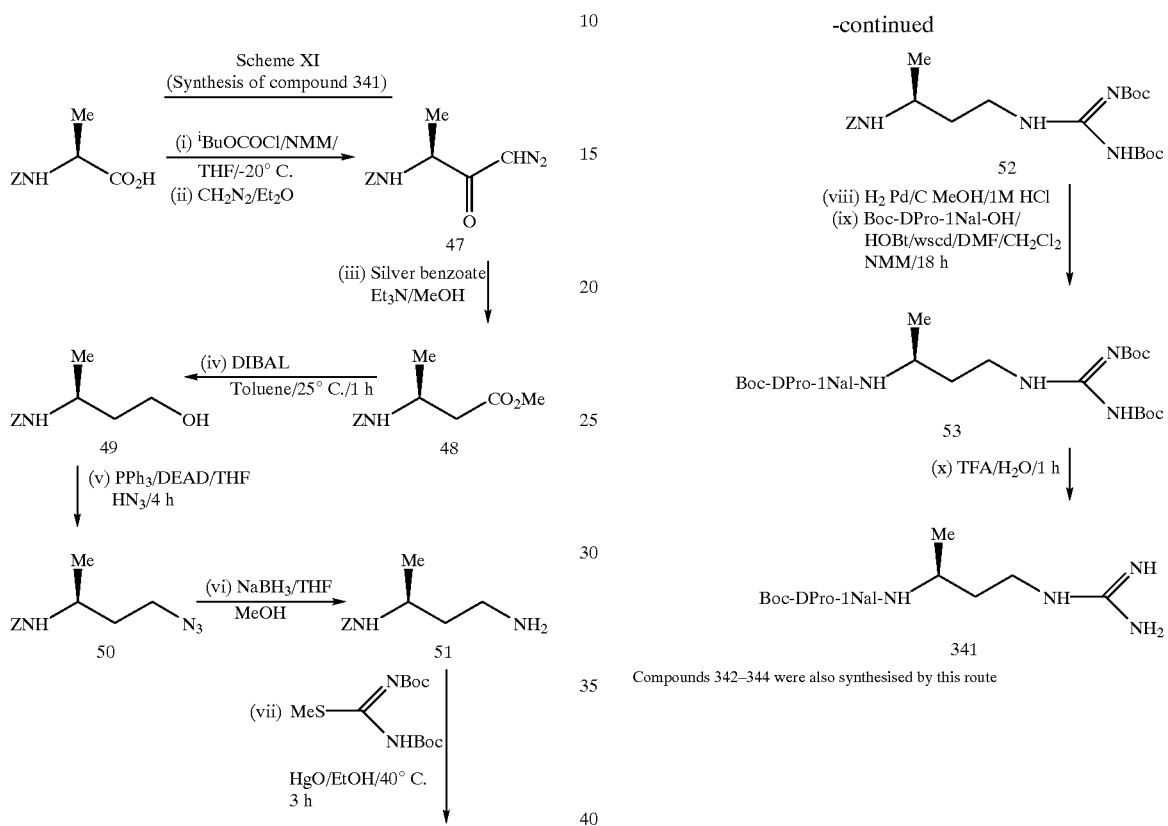
Compounds 342–344 were also synthesised by this route
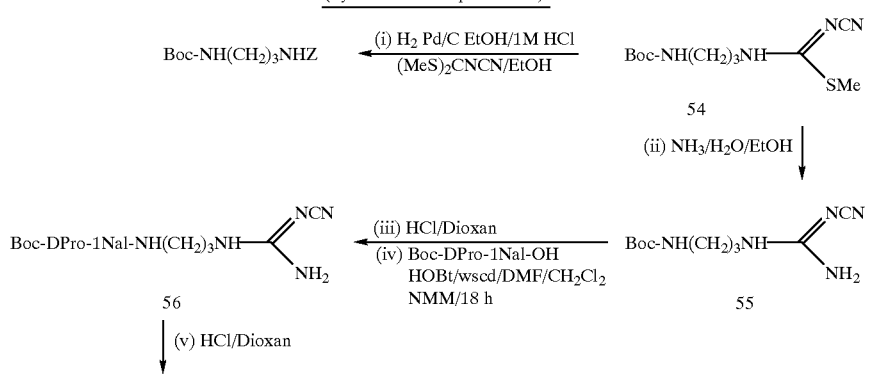

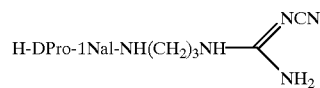
-continued
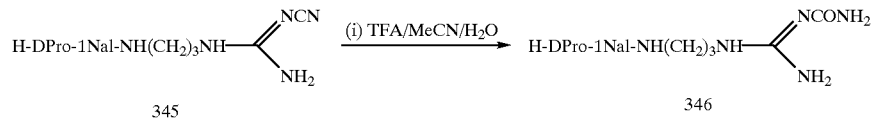
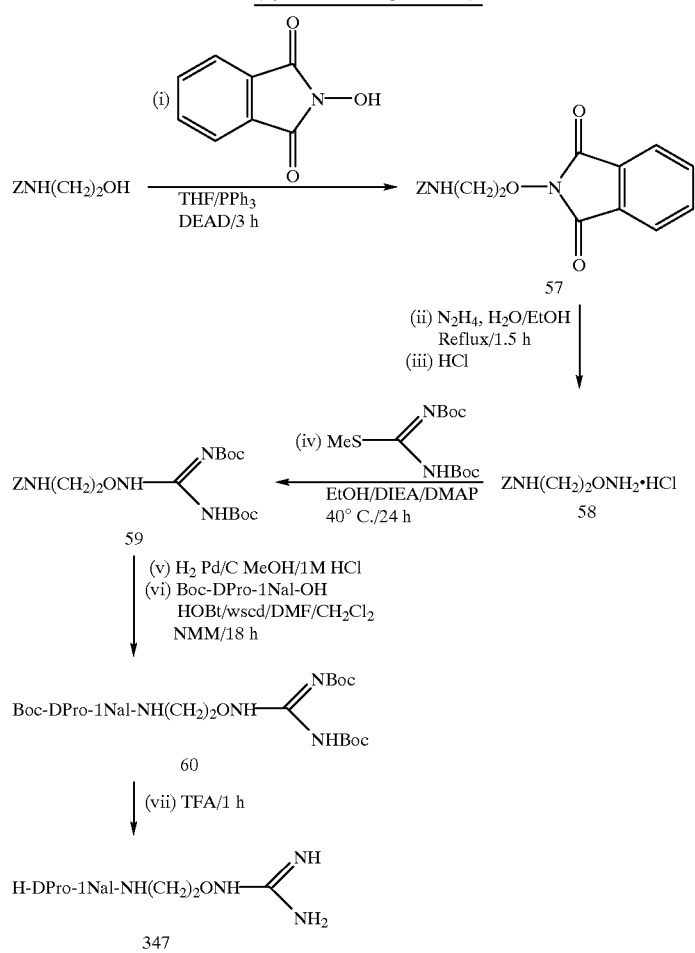

Scheme XV
(Synthesis of compound 348)
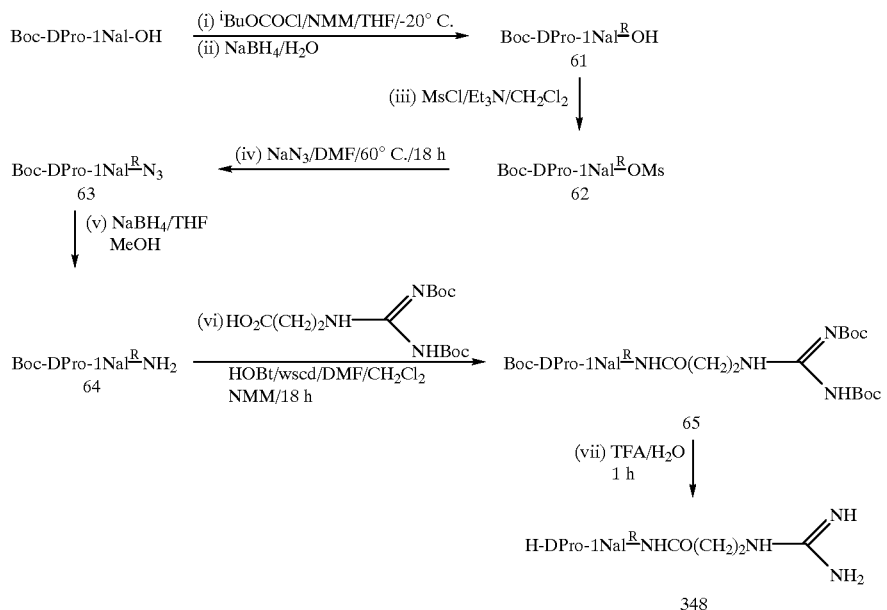
Compounds 349 and 350 were also synthesised by this route
Scheme XVI
(Synthesis of compound 351)
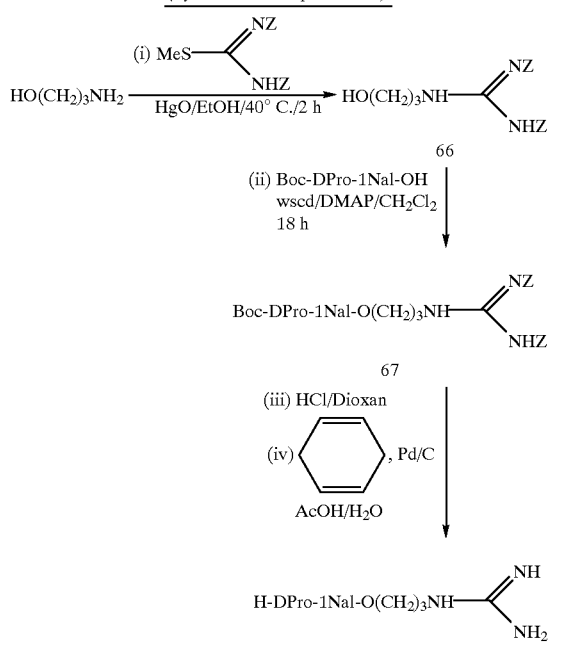
Scheme XVII
(Synthesis of compound 352)
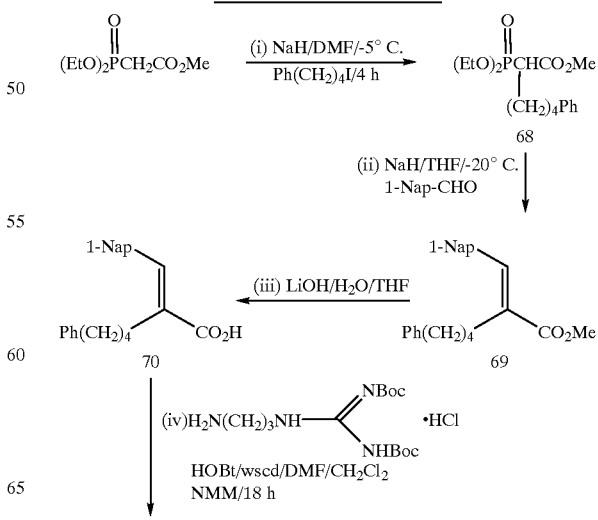

-continued
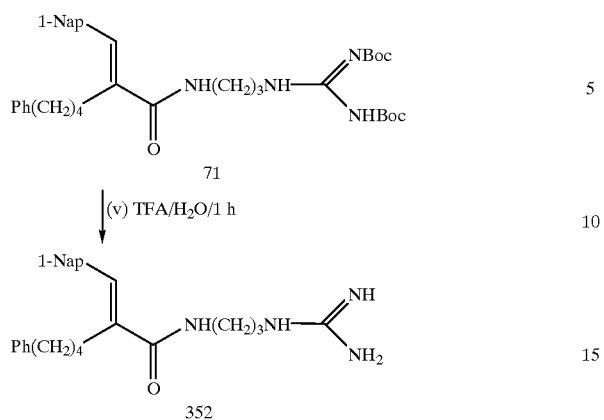
Compound 353 was also synthesised by this route
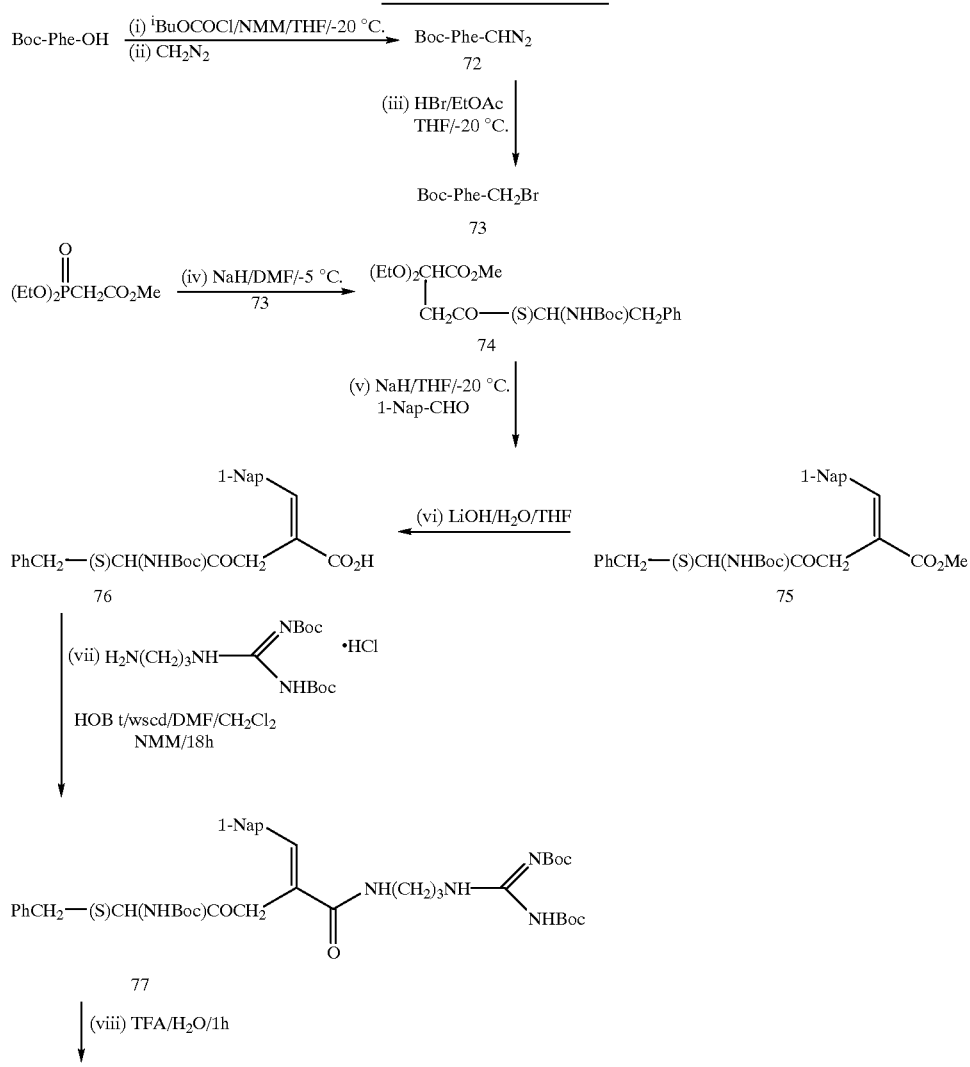

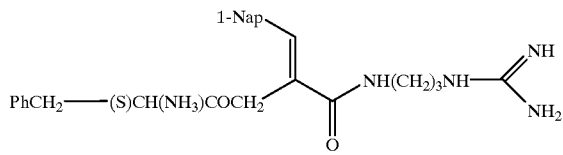
Compounds 355-357 were also synthesised by this route

TABLE 1

| | | | [M + H]⁺ |
|---|---|---|---|
| 101 | H-DPro- | Phe- | Nag | 361 |
| 102 | H-DPro- | 1Nal- | Nag | 411.2 |
| 103 | H-DPro- | Phe- | (1-Me)Nag | 375.1 |
| 104 | H-DPro- | 2Nal- | Nag | 411.2 |
| 105 | Ac- | 1Nal- | Nag | 356.2 |
| 106 | H-DPro- | 1Nal- | (5-Me)Nag | 425.2 |
| 107 | H-DPro- | D1Nal-(5-Me)Nag | | 425.3 |
| 108 | H-DPro- | D1Nal-Nag | | 411.2 |
| 109 | H- Pro- | D1Nal-Nag | | 411.2 |
| 110 | H- Pro- | 1Nal- | Nag | 411.2 |
| 111 | Z- | 1Nal- | Nag | 448.2 |
| 112 | H-DPro- | 1Nal-(1-Me)Nag | | 425.3 |
| 113 | Cpc- | 1Nal- | Nag | 410.3 |
| 114 | H-DArg- | 1Nal- | Nag | 470.5 |
| 115 | H-DPhe- | 1Nal- | Nag | 461.3 |
| 116 | H-DPic- | 1Nal- | Nag | 425.3 |
| 117 | H-(3R)Cti- | 1Nal- | Nag | 473.3 |
| 118 | H-DAha- | 1Nal- | Nag | 427.2 |
| 119 | H-DPro- | 1Nal-(7-Me)Nag | | 425.3 |
| 120 | H-(S)2Pro- | 1Nal- | Nag | 411.3 |
| 121 | H-(R)2Pro- | 1Nal- | Nag | 411.2 |
| 122 | 2-Py-CO- | 1Nal- | Nag | 419.3 |
| 123 | 3-Pyz-CO- | 1Nal- | Nag | 420.2 |
| 124 | H-DPro[R]CO-1Nal- | | Nag | 425.2 |
| 125 | 2-Piz-CO- | 1Nal- | Nag | 426.3 |
| 126 | H-3-DPal- | 1Nal- | Nag | 462.3 |
| 127 | 3-Py-CO- | 1Nal- | Nag | 419.3 |
| 128 | 3-Iqc- | 1Nal- | Nag | 469.3 |
| 129 | H-(R)Nip- | 1Nal- | Nag | 425.3 |
| 130 | H-(S)Nip- | 1Nal- | Nag | 425.3 |
| 131 | H-2Aze- | 1Nal- | Nag | 397.3 |
| 132 | Me-DPhe- | 1Nal- | Nag | 475.3 |
| 133 | H-DAla- | 1Nal- | Nag | 385.2 |
| 134 | Me- DAla- | 1Nal- | Nag | 399.5 |
| 135 | H-DTrp- | 1Nal- | Nag | 500.3 |
| 136 | H-DTyr- | 1Nal- | Nag | 477.3 |
| 137 | H-DHis- | 1Nal- | Nag | 451.3 |
| 138 | H-(4-Et)DTyr- | 1Nal- | Nag | 505.3 |
| 139 | H-DPhg- | 1Nal- | Nag | 477.3 |
| 140 | H-DCha- | 1Nal- | Nag | 467.4 |
| 141 | H-DHar- | 1Nal- | Nag | 484.3 |
| 142 | H-D1Nal- | 1Nal- | Nag | 511.3 |
| 143 | H-D2Nal- | 1Nal- | Nag | 511.3 |
| 144 | H-(4-NO₂)DPhe- | 1Nal- | Nag | 506.3 |
| 145 | H-(4-F)DPhe- | 1Nal- | Nag | 479.3 |
| 146 | H-DCit- | 1Nal- | Nag | 471.4 |
| 147 | H-DHci- | 1Nal- | Nag | 485.4 |
| 148 | H-(3R)Cdi- | 1Nal- | Nag | 479.3 |
| 149 | H-allo-DHyp- | 1Nal- | Nag | 427.2 |
| 150 | H-DHph- | 1Nal- | Nag | 475.4 |
| 151 | H-DPyr- | 1Nal- | Nag | 425.3 |
| 152 | H-DMe-Phe- | 1Nal- | Nag | 475.4 |
| 153 | H-Me-Phe- | 1Nal- | Nag | 475.4 |
| 154 | H-DAtc- | 1Nal- | Nag | 487.4 |
| 155 | H-Atc- | 1Nal- | Nag | 487.3 |
| 156 | H-Aic- | 1Nal- | Nag | 473.3 |
| 157 | H-(2-Me)DPhe-1Nal- | | Nag | 475.3 |
| 158 | H-(2-Me)Phe- | 1Nal- | Nag | 475.3 |
| 159 | Gpa- | 1Nal- | Nag | 455.3 |
| 160 | Gha- | 1Nal- | Nag | 469.3 |
| 161 | H-(4-Cl)DPhe- | 1Nal- | Nag | 495.2 |
| 162 | H-D1Tna- | 1Nal- | Nag | 515.4 |
| 163 | H-(RS)1Dhn- | 1Nal- | Nag | 521.4 |
| 164 | H-D2Dhn- | 1Nal- | Nag | 521.4 |
| 165 | Cp-CO-DPhe- | 1Nal- | Nag | 557.3 |
| 166 | H-Phe- | 1Nal- | Nag | 461.3 |
| 167 | (3R)ThiCH₂CO-1Nal- | | Nag | 487.3 |
| 168 | H-DTal- | 1Nal- | Nag | 467.3 |
| 169 | H-Aib- | 1Nal- | Nag | 399.3 |
| 170 | H-DePse(Me)- | 1Nal- | Nag | 491.3 |
| 171 | H-(1S)Cti- | 1Nal- | Nag | 473.3 |
| 172 | H-(1R)Cti- | 1Nal- | Nag | 473.3 |
| 173 | H-(2R)Cin- | 1Nal- | Nag | 459.2 |
| 174 | H-D3Bta- | 1Nal- | Nag | 517.3 |
| 175 | H-D2Pal- | 1Nal- | Nag | 462.4 |
| 176 | H-2Pal- | 1Nal- | Nag | 462.4 |
| 177 | H-D4Pal- | 1Nal- | Nag | 462.3 |

TABLE 1-continued

|     |                          |       |     | [M + H]⁺ |
|-----|--------------------------|-------|-----|----------|
| 178 | H-4Pal-                  | 1Nal- | Nag | 462.4    |
| 179 | H-DPhe[R]-               | 1Nal- | Nag | 447.2    |
| 180 | H-DGlu-                  | 1Nal- | Nag | 443.2    |
| 181 | H-DPhe-D(Me)-            | 1Nal- | Nag | 475.4    |
| 182 | H-DPhe-(Me)-             | 1Nal- | Nag | 475.4    |
| 183 | H-DLeu-                  | 1Nal- | Nag | 427.3    |
| 184 | H-DHch-                  | 1Nal- | Nag | 481.4    |
| 185 | H-DVal-                  | 1Nal- | Nag | 413.3    |
| 186 | H-DPhe[R]CO-1Nal-        |       | Nag | 475.2    |
| 187 | H-DSer(Bu)-              | 1Nal- | Nag | 457.4    |
| 188 | H-(3S)Cti-               | 1Nal- | Nag | 473.4    |
| 189 | H-(3-F)DPhe-             | 1Nal- | Nag | 479.3    |
| 190 | H-(3-F)Phe-              | 1Nal- | Nag | 479.3    |
| 191 | H-(2S)Inc-               | 1Nal- | Nag | 459.3    |
| 192 | H-(4-NH₂)DPhe-1Nal-      |       | Nag | 476.3    |
| 193 | H-4-Gph-                 | 1Nal- | Nag | 518.3    |
| 194 | H-DthPse(Me)-            | 1Nal- | Nag | 491.3    |
| 195 | H-thPse(Me)-             | 1Nal- | Nag | 491.3    |
| 196 | H-DthPse(Bu)-            | 1Nal- | Nag | 533.4    |
| 197 | H-thPse(Bu)-             | 1Nal- | Nag | 533.4    |
| 198 | H-(4-CF₃)-DPhe-1Nal-     |       | Nag | 529.3    |
| 199 | H-(4-CF₃)Phe-            | 1Nal- | Nag | 529.3    |
| 200 | H-ePse(Me)-              | 1Nal- | Nag | 491.3    |
| 201 | H-DthPse-                | 1Nal- | Nag | 477.3    |
| 202 | H-thPse-                 | 1Nal- | Nag | 477.3    |
| 203 | H-Dph-                   | 1Nal- | Nag | 568.3    |
| 204 | H-((3R)-Ph)-DPro-1Nal-   |       | Nag | 487.4    |
| 205 | H-((3R)-Ph)Pro-1Nal-     |       | Nag | 487.4    |
| 206 | H-((3S)-Ph)DPro-1Nal-    |       | Nag | 487.4    |
| 207 | H-((3S)-Ph)Pro-          | 1Nal- | Nag | 487.4    |
| 208 | H-(4-I)DPhe-             | 1Nal- | Nag | 587.2    |
| 209 | H-DChg-                  | 1Nal- | Nag | 453.2    |
| 210 | H-DePse-                 | 1Nal- | Nag | 477.4    |
| 211 | H-ePse-                  | 1Nal- | Nag | 477.4    |
| 212 | H-(2,4-Cl₂)DPhe-         | 1Nal- | Nag | 529.2    |
| 213 | H-(2,4-Cl₂)Phe-          | 1Nal- | Nag | 529.2    |
| 214 | H-(3,4-Cl₂)DPhe-         | 1Nal- | Nag | 529.2    |
| 215 | H-(3,4-Cl₂)Phe-          | 1Nal- | Nag | 529.2    |
| 216 | H-3-DGph-                | 1Nal- | Nag | 518.3    |
| 217 | H-3-Gph-                 | 1Nal- | Nag | 518.3    |
| 218 | H-DePse(Bu)-             | 1Nal- | Nag | 533.4    |
| 219 | H-ePse(Bu)-              | 1Nal- | Nag | 533.4    |
| 220 | H-(4-CN)DPhe-            | 1Nal- | Nag | 486.4    |
| 221 | H-(4-CN)Phe-             | 1Nal- | Nag | 486.3    |
| 222 | H-DCpg-                  | 1Nal- | Nag | 439.3    |
| 223 | H-Cpg-                   | 1Nal- | Nag | 439.4    |
| 224 | H-(4-AcNH)DPhe-1Nal-     |       | Nag | 518.2    |
| 225 | H-((3'R)-Me)DPhe-1Nal-   |       | Nag | 475.4    |
| 226 | H-((3'S)-Me)DPhe-1Nal-   |       | Nag | 475.2    |
| 227 | H-DPro-                  | 1Tna- | Nag | 415.3    |
| 228 | H-DArg-                  | Phe-  | Nag | 420.2    |
| 229 | H-Arg-                   | Phe-  | Nag | 420.2    |
| 230 | H-Aha-                   | Lys-  | Nag | 358.2    |
| 231 | H-DPro-DePse(Me)-        |       | Nag | 391.3    |
| 232 | H-DPro-ePse(Me)-         |       | Nag | 391.3    |
| 233 | H-DPro-DthPse(Me)-       |       | Nag | 391.3    |
| 234 | H-DPro-thPse(Me)-        |       | Nag | 391.3    |
| 235 | H-DPro-DLAmp-            |       | Nag | 459.4    |
| 236 | H-DLys-Phe-              |       | Nag | 392.2    |
| 237 | H-DPro-De2Nse(Me)-       |       | Nag | 441.1    |
| 238 | H-DPro-e2Nse(Me)-        |       | Nag | 441.1    |
| 239 | H-DPro-thNse(Me)-        |       | Nag | 441.4    |
| 240 | H-DPro-DthNse(Me)-       |       | Nag | 441.4    |
| 241 | H-DPro-DthPse-           |       | Nag | 377.3    |
| 242 | H-DPro-thPse-            |       | Nag | 377.3    |
| 243 | H-DPro-DLth1Nse(Me)-     |       | Nag | 441.4    |
| 244 | H-DPro-Cha-              |       | Nag | 367.3    |
| 245 | H-DPro-1Dhn-             |       | Nag | 421.4    |
| 246 | H-DPro-Ada-              |       | Nag | 419.3    |
| 247 | H-DPro-Trp-              |       | Nag | 400.2    |
| 248 | H-DPro-(4-F)Phe-         |       | Nag | 379.2    |
| 249 | H-DPro-Aha-              |       | Nag | 327.3    |
| 250 | H-DPro-Ser(Bu)-          |       | Nag | 357.3    |
| 251 | H-DPro-Leu-              |       | Nag | 327.3    |
| 252 | H-DPro-(5F)Phe-          |       | Nag | 451.2    |
| 253 | H-DPhe-Cha-              |       | Nag | 417.3    |
| 254 | H-DPro-Hch-              |       | Nag | 381.3    |

TABLE 1-continued

|   |   |   |   | [M + H]⁺ |
|---|---|---|---|---|
| 255 | H-DPro-(3S)Cti- | | Nag | 373.2 |
| 256 | H-DPhe-1Dhn- | | Nag | 471.3 |
| 257 | H-DArg-1Dhn- | | Nag | 480.4 |
| 258 | H-DPro-2Dhn- | | Nag | 421.3 |
| 259 | H-DPro-Ser(Bzl)- | | Nag | 391.3 |
| 260 | H-DPro-1Tna[R]CO- | | Nag | 429.4 |
| 261 | H-DPro-1Dhn[R]CO- | | Nag | 435.4 |
| 262 | H-DPro-DLMe-Phe- | | Nag | 375.2 |
| 263 | H-DHar-1Dhn- | | Nag | 494.5 |
| 264 | H-DAha-1Dhn- | | Nag | 437.4 |
| 265 | H-DPro-1Nal[R]CO- | | Nag | 425.3 |
| 266 | H-DIle-1Nal- | | Nag | 427.3 |
| 267 | (2-MeO)PhCH=CHCO- | | Nag | 277.2 |
| 268 | PhCH₂CO- | | Nag | 217.1 |
| 269 | Ph(CH₂)₂CO- | | Nag | 249.2 |
| 270 | Ph(CH₂)₃CO- | | Nag | 263.2 |
| 271 | 2-Nap-CH₂CO- | | Nag | 285.1 |
| 272 | 1-Nap-CH₂CO- | | Nag | 285.1 |
| 273 | 1-Nap-CH=CHCO- | | Nag | 279.1 |
| 274 | 2-Nap-CH=CHCO- | | Nag | 279.2 |
| 275 | 2-Nap-(CH₂)₂CO- | | Nag | 275 |
| 276 | c(2-MeO)Ph-CH=CHCO- | | Nag | 277.2 |
| 277 | Ph-CH=CHCO- | | Nag | 247.2 |
| 278 | (4-Cl)Ph-CH=CHCO- | | Nag | 281.1 |
| 279 | (2,3-(MeO)₂Ph)-CH=CHCO- | | Nag | 307.2 |
| 280 | Ch-CH=CHCO- | | Nag | 253.2 |
| 281 | (2-NO₂)Ph-CH=CHCO- | | Nag | 292.2 |
| 282 | Ph-C≡C CO- | | Nag | 245.1 |
| 283 | Cud-CH=CHCO- | | Nag | 323.3 |
| 284 | Ph-CH=CHSO₂ | | Nag | 283.1 |
| 285 | | Dnma - | Nag | 439.3 |
| 286 | Ph-CH=C(Me)CO-Nag | | | 261.2 |
| 287 | Ph-CH=C(F)CO- | | Nag | 265.1 |
| 288 | 4Qui-CH=CHCO- | | Nag | 298.2 |
| 289 | 9-Ant-CH=CHCO- | | Nag | 347.2 |
| 290 | (3,4-MeO)₂)Ph-CH=CHCO- | | Nag | 307.1 |
| 291 | (F5)Ph-CH=CHCO- | | Nag | 337.1 |
| 292 | (3,5-(MeO)₂)-Ph-CH=CHCO- | | Nag | 307.2 |
| 293 | 2-Fen-CH CHCO- | | Nag | 335.2 |
| 294 | (2,5-(MeO)₂)Ph-CH=CHCO- | | Nag | 307.2 |
| 295 | (2,4-(MeO)₂)Ph-CH=CHCO- | | Nag | 307.2 |
| 296 | (3,4-Cl₂)Ph-CH=CHCO- | | Nag | 315.1 |
| 297 | (3-NO₂, 4-Cl)Ph-CH=CHCO- | | Nag | 326.1 |
| 298 | (2,4-Cl₂)Ph-CH=CHCO- | | Nag | 315.1 |
| 299 | (4-MeO)Ph-CH=CHCO- | | Nag | 277.2 |
| 300 | (4-N(Me)₂)Ph-CH=CHCO- | | Nag | 290.2 |
| 301 | 1-(4-N(Me)₂)Ph-CH=CHCO- | | Nag | 340.3 |
| 302 | (4-Br)Ph-CH=CHCO- | | Nag | 327.1 |
| 303 | (4-NO₂)Ph-CH=CHCO- | | Nag | 292.2 |
| 304 | (4-CF₃)Ph-CH=CHCO- | | Nag | 315.2 |
| 305 | (4-Me)Ph-CH=CHCO- | | Nag | 261.2 |
| 306 | (4-Ph)Ph-CH=CHCO- | | Nag | 323.2 |
| 307 | (2-OH)Ph-CH=CHCO- | | Nag | 263.2 |
| 308 | (4-OH)Ph-CH=CHCO- | | Nag | 263.2 |
| 309 | | Ph(CH₂)₃CO- | Nag | 460.2 |
| 310 | | Ch(CH₂)CO- | Nag | 466.4 |
| 311 | 1-(4-MeO)Nap-CH=CHCO- | | Nag | 327.2 |
| 312 | 2-Thp-CH=CHCO- | | Nag | 253.1 |
| 313 | 3-Thp-CH=CHCO- | | Nag | 253.1 |
| 314 | Coc-CH=CHCO- | | Nag | 281.3 |
| 315 | Dna-CH=CHCO- | | Nag | 307.3 |
| 316 | (4-NH₂)Ph-CH=CHCO- | | Nag | 262.2 |
| 317 | (4-ZNH)Ph-CH=CHCO- | | Nag | 396.2 |
| 318 | Ph-CH=C(Ph)CO- | | Nag | 323.2 |
| 319 | 9-(10-Cl)Ant-CH=CHCO- | | Nag | 381.2 |
| 320 | 1-(2-MeO)Nap-CH=CHCO- | | Nag | 327.1 |
| 321 | 1-Fen-CH=CHCO- | | Nag | 335.2 |
| 322 | 9-Fen-CH=CHCO- | | Nag | 335.2 |
| 323 | (Pr)₂CHCH=CHCO- | | Nag | 269.3 |
| 324 | 1(4-F)Nap-CH=CHCO- | | Nag | 315.2 |
| 325 | Cdd-CH=CHCO- | | Nag | 337.3 |
| 326 | HO₂CCH₂-(4-I)DPhe- | 1Nal- | Nag | 645.1 |
| 327 | HO₂CCH₂-DIle- | 1Nal- | Nag | 485.2 |
| 328 | HO₂CCH₂-DPro- | 1Nal- | Nag | 469.3 |
| 329 | Ms-DIle- | 1Nal- | Nag | 505.4 |
| 330 | Ms(4-I)DPhe- | 1Nal- | Nag | 665.2 |
| 331 | Ac-DIle- | 1Nal- | Nag | 469.4 |

TABLE 1-continued

| | | | | [M + H]⁺ |
|---|---|---|---|---|
| 332 | Ac(4-I)DPhe- | 1Nal- | Nag | 629.1 |
| 333 | H-DPro- | 1Nal-((3R,S)-OH) | Nag | 427.2 |
| 334 | H-DIle- | 1Nal-((3R,S)-OH) | Nag | 443.3 |
| 335 | H-(4-NO₂)DPhe- | 1Nal-((3R,S)-OH) | Nag | 522.2 |
| 336 | H-(4-Cl)DPhe- | 1Nal-((3R,S)-OH) | Nag | 511.3 |
| 337 | H-(4-Cl)DPhe- | 1Nal-((3R,S-OMe) | Nag | 525.4 |
| 338 | H-DPro- | 1Nal-(3-CO) | Nag | * |
| 339 | H-DPro- | 1Nal-(3R-Me) | Nag | 425.3 |
| 340 | H-DPro- | 1Nal-(3S-Me) | Nag | 425.3 |
| 341 | H-DPro- | 1Nal-(2S-Me) | Nag | 425.3 |
| 342 | H-DPro- | 1Nal-(2R-Me) | Nag | 425.2 |
| 343 | H-DPro- | 1Nal-(4S-Me) | Nag | 425.3 |
| 344 | H-DPro- | 1Nal-(4R-Me) | Nag | 425.3 |
| 345 | H-DPro- | 1Nal-(7-CN) | Nag | 436.1 |
| 346 | H-DPro- | 1Nal-(7-CONH₂) | Nag | 454.1 |
| 347 | H-DPro- | 1Nal-NH(CH₂)₂ONHC(=NH)NH₂ | | 413.2 |
| 348 | H-DPro- | 1Nal[R](2-CO) | Nag | 562.3 |
| 349 | H-(4-I)DPhe-1Nal[R](2-CO) | | Nag | 587.3 |
| 350 | H-DIle- | 1Nal[R](2-CO) | Nag | 587.3 |
| 351 | H-DPro- | 1Nal-O(CH₂)₃NHC(=NH)NH₂ | | 412.2 |
| 352 | 1-Nap-CH=C((CH₂)₄Ph)CO- | | Nag | 429.3 |
| 353 | 1-Nap-CH=C((CH₂)₃Ph)CO- | | Nag | 415.2 |
| 354 | 1-Nap-CH=C[CH₂CO-(S)CH(NH₂)CH₂Ph]CO-Nag | | | 458.2 |
| 355 | 1-Nap-CH=C[CH₂CO-(R)CH(NH₂)CH₂Ph]CO-Nag | | | 458.2 |
| 356 | 1-Nap-CH=C[(CH₂)₂(R)CH(NH₂)CH₂Ph]CO-Nag | | | 444.3 |
| 357 | 1-Nap-CH=C[(CH₂)₂(S)CH(NH₂)CH₂Ph]CO-Nag | | | 444.3 |
| 358 | H-DPro- | Phe- | Agm | 375 |
| 359 | H-DPro- | Phe(1-Me)Agm | | 459 |
| 360 | H-DPro- | Phe(1-Hx)Agm | | 389.2 |
| 361 | H-DTyr(Et)- | Phe- | Agm | 469.4 |
| 362 | H-DTyr- | Phe- | Agm | 441.3 |
| 363 | H-DCha- | Phe- | Agm | 431.4 |
| 364 | H-DArg- | Phe- | Agm | 434.2 |
| 365 | H-DIle- | 1Nal- | Agm | 441.3 |
| 366 | H-(4-I)DPhe-1Nal- | | Agm | 601.1 |

\* No [M + H]⁺ observed

| ABBREVIATIONS | |
|---|---|
| Ac | Acetyl |
| AcOH | Acetic acid |
| Ada | Adamantylalanine |
| Aib | 2-Amino-isobutyric acid |
| Aic | 2-Aminoindan-2-carboxylic acid |
| Agm | Agmatine |
| Amp | 2-Amino-3-(7-methoxy-4-coumaryl) propionic acid |
| Ant | Anthracene |
| Atc | 2-Aminotetralin-2-carboxylic acid |
| Aze | Azetidine-2-carboxylic acid |
| Boc | tert-Butyloxycarbonyl |
| Bta | Benzothienylalanine |
| Bu | Butyl |
| Bzl | Benzyl |
| Cdi | Carboxydecahydroisoquinoline |
| Cdd | Cyclododecyl |
| Cha | Cyclohexylalanine |
| Ch | Cyclohexyl |
| Chg | Cyclohexyglycine |
| Cin | Carboxyindoline |
| Cit | Citrulline |
| Coc | Cyclooctyl |
| Cp | Cyclopentyl |
| Cpc | Cyclopentane carboxylic acid |
| Cpr | Cyclopropyl |
| Cti | Carboxy-1,2,3,4-tetrahydroisoquinoline |
| Cud | Cycloundecyl |
| DEAD | Diethyl azodicarboxylate |
| Dhn | Decahydronaphthylalanine |
| DIBAL | Diisobutylaluminium hydride |
| DIEA | N,N-Diisopropylethylamine |
| DMAP | 4-Dimethylaminopyridine |

-continued

| ABBREVIATIONS | |
|---|---|
| DMF | Dimethylformamide |
| Dna | Decahydronaphthyl |
| Dnma | Di-(1-naphthylmethyl) acetic acid |
| DPPA | Diphenylphosphoryl azide |
| Dpn | α,β-Dehydrophenylalanine |
| e | erythro |
| Et | Ethyl |
| EtOAc | Ethyl acetate |
| EtOH | Ethanol |
| FAB | Fast atom bombardment |
| Fen | Fluorenyl |
| Fmoc | 9-Fluorenylmethoxycarbonyl |
| Gha | 6-Guanidino hexanoic acid |
| Gpa | 5-Guanidino pentanoic acid |
| Gph | Guanidinophenylalanine |
| Har | Homoarginine |
| Hci | Homocitrulline |
| Hch | Homocyclohexylalanine |
| HoBT | 1-Hydroxybenzotriazole |
| Hph | Homophenylalanine |
| Hplc | High performance liquid chromatography |
| Hx | n-Hexyl |
| Hyp | Hydroxyproline |
| Inc | Indoline carboxylic acid |
| Iqc | Isoquinoline carboxylic acid |
| Me | Methyl |
| MeCN | Acetonitrile |
| MeOH | Methanol |
| mplc | Medium pressure liquid chromatography |
| Ms | Mesyl |
| Nag | Noragmatine |
| Nal | Naphthylalanine |

-continued

ABBREVIATIONS

| | |
|---|---|
| Nap | Naphthyl |
| Nip | Nipecotic acid |
| NMM | N-Methylmorpholine |
| Nse | Naphthylserine |
| ONSu | Hydroxysuccinimide |
| Pal | Pyridylalanine |
| Petrol | Petroleum ether 60–80° C. |
| Phg | Phenylglycine |
| Pic | Pipecolinic acid |
| Piz | Piperazinyl |
| PPTS | Pyridinium p-toluenesulphonate |
| Pr | Propyl |
| Pse | Phenylserine |
| Py | Pyridyl |
| Pyr | Pyroglutamic acid |
| Pyz | Pyrazinyl |
| Qui | Quinoline |
| [R] or R | Reduced isostere -CH$_2$- replacing -CO-; eg. BocNHCH$_2$CH$_2$OH=BocGly$^R$OH |
| Tal | 3(2'-Thienyl)alanine |
| TFA | Trifluoroacetic acid |
| th | threo |
| THF | Tetrahydrofuran |
| Thi | 1,2,3,4-Tetrahydroisoquinoline |
| Thp | Thiophene |
| tlc | Thin layer chromatography |
| Tna | 1,2,3,4-Tetrahydronaphthylalanine |
| wscd | Water soluble carbodiimide |
| Z | Benzyloxycarbonyl |

References to test methods:

In vitro tests use standard published kininogenase-inhibition assays based on chromogenic substrates (see e.g. Johansen et al. Int. J. Tiss. Reac. 1986, 8, 185; Shori et al. Biochem. Pharmacol. 1992, 43, 1209; Sturzebecher et al. Biol. Chem. Hoppe-Seyler, 1992, 373, 1025). The inhibitory constant Ki is determined using Dixon plots (Dixon, Biochem. J. 1953, 55, 170).

We claim:

1. A kininogenase inhibiting peptide having an in vitro Ki values of $10^{-3}$ to $10^{-9}$ M in a kininogenase inhibition assay and having the structure

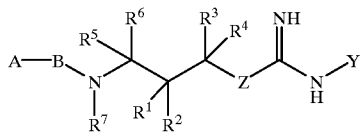

wherein:

A is an α-amino acid of D- or L-configuration or an α-imino acid of D- or L-configuration;

B is an α-amino add of D or L configuration selected from the group consisting of: Ada; Aha; Cha; 1-Dhn; 2-Dhn; homo-1-Dhn; Hch; Leu; 1-Nal; 2-Nal; homo-1-Nal; Nse; Phe; 4-F-Phe; pentafluoro -Phe; Ser(O"Bu); Ser (OBn); Trp; 1-Tna; and homo-1-Tna;

Y is selected from —H, —NO$_2$, and —CN;

Z is selected from —CH$_2$—, 13 NH—, —S— and —O—;

R$^7$ is independently selected from H and C$_1$ to C$_6$ alkyl;

R$^5$ and R$^6$ are independently selected from H and C$_1$ to C$_6$ alkyl; and

R$^1$, R$^2$, R$^3$, R$^4$, are independently selected from H, C$^1$ to C$_6$ alkyl, —OH, and C$_1$ to C$_6$ alkoxy; or either one of CR$^1$R$^2$ or CR$^3$R$^4$ constitutes a carbonyl group or a C$_3$–C$_6$ cycloalkyl group.

2. A kininogenase inhibiting peptide according to claim 1 wherein A is an α-amino acid with D or L configuration selected from the group consisting of: Aib; Aic; Ala; Aha; Apa; Arg; Atc; Aze; Bta; Cdi; Cha; Cin; Cit; Cpg; 1-Dhn; 2-Dhn; Dpn; Glu; 4-Gph; 3-Gph; Har; Hch; Hci; His; Hph; Hyp; Ile; Leu; Lys; 1-Nal; 2-Nal; 2-Pal; 4Pal; Phe; 4-CF$_3$-Phe; 4-Cl-Phe; 4-CN-Phe; 4-F-Phe; pentafluoro-Phe; 2Me-Phe; 4-NO$_2$-Phe; 4-NH$_2$-Phe; 2-4-Cl$_2$-Phe; 3,4-Cl$_2$-Phe or other substituted Phe; Phg; Pic; Pro; 3-Ph-Pro; Pse; Pse(OR) where R=C$_1$ to C$_{10}$ alkyl; Pyr, Ser; Ser(O"Bu); Tal; Tic; α-Tna; Trp; Tyr; Tyr(Et); and Val.

3. A kininogenase inhibiting peptide according to claim 1 wherein the amide function —CONH— between the residues can be replaced by a peptide mimetic selected from the group consisting of —CH═CH—; —CF═CH—; —CHNR$^8$—, wherein R$^8$ is selected from the group consisting of H, C$_1$–C$_6$ alkyl and OH; —COCH$_2$—; —CH(OH) CH$_2$—; —CH$_2$O; —CH$_2$S—; —CHSO$_x$—, wherein x=1 or 2; —NHCO—; and —CH$_2$CH$_2$—.

4. A kininogenase inhibiting peptide according to claim 1 wherein R$^1$ to R$^7$ are hydrogen.

5. A kininogenase inhibiting peptide according to claim 1 wherein at least one of R$^1$ to R$^6$ is C$_1$ to C$_6$ alkyl, the remainder being hydrogen.

6. A kininogenase inhibiting peptide according to claim 1, wherein B is 1-Nal.

7. A kininogenase inhibiting peptide according to claim 6, wherein R$^1$ to R$^7$ are hydrogen.

8. A kininogenase inhibiting peptide according to claim 1, wherein B is 1-Dhn.

9. A kininogenase inhibiting peptide according to claim 8, wherein R$^1$ to R$^7$ are hydrogen.

10. A kininogenase inhibiting peptide according to claim 1 wherein A is substituted with an N-terminal group selected from the group consisting of C$_1$–C$_6$ acyl or aromatic acyl; C$_1$–C$_6$ alkyl sulphonyl; C$_3$–C$_{10}$alkyl; amino-acyl; alkyloxy-carbonyl; aryloxycarbonyl; HO$_2$C(CH$_2$)$_n$—, where n=1 to 3, and esters and amides thereof.

11. A kininogenase inhibiting peptide according to claim 1 wherein B is substituted at the α-nitrogen with C$_1$–C$_6$ alkyl.

12. A kininogenase inhibiting peptide according to claim 1, wherein A has a D configuration.

13. A kininogenase inhibiting peptide according to claim 1, wherein B has a L configuration.

14. A pharmaceutical preparation containing a kininogenase-inhibiting amount of a kininogenase inhibiting peptide according to claim 1 and a pharmaceutically acceptable carrier.

15. A method of treatment of a condition selected from the group consisting of: inflammation, smooth muscle spasm, hypotension, edema, pain and irritation, comprising the step of administering to a patient suffering from said condition an effective amount of a kininogenase inhibiting compound according to claim 1.

16. A method of practicing male contraception comprising the step of administering to an individual an effective amount of a kininogenase inhibiting compound according to claim 1.

17. A method according to claim 15 where the condition treated is allergic inflammation.

18. A method according to claim 15 where the condition treated is pancreatitis.

19. A method according to claim 15 where the condition treated is chronic hypotension.

* * * * *

UNITED STATES PATENT AND TRADEMARK OFFICE
CERTIFICATE OF CORRECTION

PATENT NO. : 6,096,712
DATED : August 1, 2000
INVENTOR(S) : Szelke et al.

Page 1 of 1

It is certified that error appears in the above-identified patent and that said Letters Patent is hereby corrected as shown below:

Title page,
Item [73] Assignee: Ferring B.V., Hoofdorp, Netherlands

Column 5,
Lines 37-47, replace the diagram with the following diagram:

i)

C is:

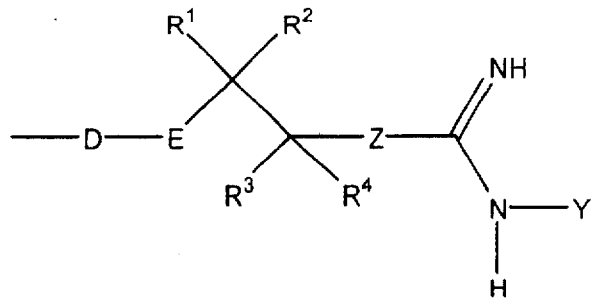

Signed and Sealed this

Fifth Day of March, 2002

Attest:

JAMES E. ROGAN
Attesting Officer — Director of the United States Patent and Trademark Office